United States Patent
Fletcher et al.

(10) Patent No.: US 11,541,396 B2
(45) Date of Patent: Jan. 3, 2023

(54) POINT-OF-CARE DIAGNOSTIC SYSTEMS AND CONTAINERS FOR SAME

(71) Applicant: IDEXX Laboratories, Inc., Westbrook, ME (US)

(72) Inventors: Michael Fletcher, Portland, ME (US); David L. Connolly, Eliot, ME (US); Anne Leavitt, Gorham, ME (US); Matthew M. Furtney, Freeport, ME (US); Christopher Labak, Brookline, NH (US); Christopher Aiston, Mont Vernon, NH (US); Daniel O'Sullivan, Mont Vernon, NH (US)

(73) Assignee: IDEXX Laboratories, Inc., Westbrook, ME (US)

( * ) Notice: Subject to any disclaimer, the term of this patent is extended or adjusted under 35 U.S.C. 154(b) by 585 days.

(21) Appl. No.: 15/941,596

(22) Filed: Mar. 30, 2018

(65) Prior Publication Data

US 2019/0299213 A1     Oct. 3, 2019

(51) Int. Cl.
*B01L 3/00* (2006.01)
*H04N 5/225* (2006.01)
(Continued)

(52) U.S. Cl.
CPC .............. *B01L 3/52* (2013.01); *B01L 3/0293* (2013.01); *B01L 9/00* (2013.01); *G01N 33/4875* (2013.01);
(Continued)

(58) Field of Classification Search
CPC .... B01L 3/52; B01L 3/0293; B01L 3/502715; B01L 9/00; B01L 2200/16;
(Continued)

(56) References Cited

U.S. PATENT DOCUMENTS

| 3,909,136 A | 9/1975 | Thomas |
| 4,387,164 A | 6/1983 | Hevey et al. |

(Continued)

FOREIGN PATENT DOCUMENTS

| EP | 0284024 A2 | 9/1988 |
| EP | 2194385 A1 | 6/2010 |

(Continued)

OTHER PUBLICATIONS

Partial International Search Report dated May 21, 2019 by the European Patent Office acting as the International Searching Authority in corresponding International Application No. PCT/US2019/026405.

(Continued)

*Primary Examiner* — Benjamin R Whatley
(74) *Attorney, Agent, or Firm* — Carter, DeLuca & Farrell LLP

(57) ABSTRACT

The present disclosure relates to a medical diagnostic system. In various embodiments, the system includes a housing, a first receptacle in the housing for receiving a reagent container, a second receptacle in the housing for receiving a working fluid and waste container, where the second receptacle is larger than the first receptacle, two reagent access needles positioned and fixed within the first receptacle with each of the two reagent access needles being substantially horizontal to horizontally access the reagent container, and a working fluid access needle and a waste access needle positioned and fixed within the second receptacle with the working fluid access needle and the waste access needle being substantially horizontal to horizontally access the working fluid and waste container.

19 Claims, 20 Drawing Sheets

(51) Int. Cl.
*B01L 3/02* (2006.01)
*B01L 9/00* (2006.01)
*G01N 35/10* (2006.01)
*G01N 33/487* (2006.01)

(52) U.S. Cl.
CPC ......... *G01N 35/1002* (2013.01); *H04N 5/225* (2013.01); *B01L 3/502715* (2013.01); *B01L 2200/16* (2013.01); *B01L 2300/021* (2013.01); *B01L 2300/0627* (2013.01); *B01L 2300/0672* (2013.01); *B01L 2300/0809* (2013.01); *B01L 2300/0851* (2013.01); *B01L 2300/0858* (2013.01); *G01N 35/1079* (2013.01)

(58) Field of Classification Search
CPC ....... B01L 2300/021; B01L 2300/0627; B01L 2300/0672; B01L 2300/0809; B01L 2300/0851; B01L 2300/0858; G01N 33/4875; G01N 35/1002; G01N 35/1079; H04N 5/225
See application file for complete search history.

(56) References Cited

U.S. PATENT DOCUMENTS

| | | | |
|---|---|---|---|
| 5,074,658 A | 12/1991 | Tavlarides et al. | |
| 5,171,538 A * | 12/1992 | Tremmel | G01N 35/1002 422/547 |
| 5,262,329 A | 11/1993 | Carver, Jr. | |
| 5,316,725 A | 5/1994 | Carver, Jr. et al. | |
| 5,316,951 A | 5/1994 | Carver, Jr. et al. | |
| 5,380,491 A | 1/1995 | Carver, Jr. et al. | |
| 5,413,732 A | 5/1995 | Buhl et al. | |
| 5,463,228 A | 10/1995 | Krause | |
| 5,486,477 A | 1/1996 | Carver, Jr. | |
| 5,728,351 A | 3/1998 | Carver, Jr. | |
| 5,840,254 A | 11/1998 | Carver, Jr. et al. | |
| 6,391,263 B1 | 5/2002 | Mishima et al. | |
| 6,812,032 B1 | 11/2004 | Carver, Jr. et al. | |
| 6,857,530 B2 * | 2/2005 | Yourist | B65D 21/0202 215/10 |
| 6,887,429 B1 | 5/2005 | Marshall et al. | |
| 6,979,569 B1 | 12/2005 | Carver, Jr. et al. | |
| 7,294,307 B2 | 11/2007 | Carver, Jr. | |
| 7,324,194 B2 | 1/2008 | Roche et al. | |
| 7,499,581 B2 | 3/2009 | Tribble et al. | |
| 7,873,483 B2 | 1/2011 | Miyamoto et al. | |
| 7,982,201 B2 | 7/2011 | Bryant et al. | |
| 8,086,411 B2 | 12/2011 | Yoshida et al. | |
| 8,088,593 B2 | 1/2012 | Burd et al. | |
| 8,161,810 B2 | 4/2012 | Cadieux et al. | |
| 8,381,581 B2 | 2/2013 | Walsh et al. | |
| 8,460,528 B2 | 6/2013 | Pollack et al. | |
| 8,668,869 B2 | 3/2014 | Hirayama | |
| 8,679,425 B2 | 3/2014 | Ueda et al. | |
| 9,213,043 B2 | 12/2015 | Cook et al. | |
| 9,222,821 B2 | 12/2015 | Walsh et al. | |
| 9,233,371 B2 | 1/2016 | Nakamura et al. | |
| 9,322,834 B2 | 4/2016 | Hirayama et al. | |
| 2005/0074361 A1 | 4/2005 | Tanoshima et al. | |
| 2006/0105359 A1 * | 5/2006 | Favuzzi | B01L 3/508 435/6.19 |
| 2011/0014095 A1 * | 1/2011 | Ueda | B01L 3/527 422/429 |
| 2011/0207621 A1 | 8/2011 | Montagu et al. | |
| 2012/0309636 A1 | 12/2012 | Gibbons et al. | |
| 2014/0267695 A1 | 9/2014 | Scordato et al. | |
| 2015/0074361 A1 | 3/2015 | Hughes et al. | |
| 2015/0316529 A1 | 11/2015 | Choi et al. | |
| 2016/0263576 A1 * | 9/2016 | Sattler | G01N 35/00663 |
| 2016/0266155 A1 * | 9/2016 | Brennan | B01L 3/50853 |

FOREIGN PATENT DOCUMENTS

| | | |
|---|---|---|
| JP | S6242334 A | 2/1987 |
| JP | H03176664 A | 7/1991 |
| JP | 2008203277 A | 9/2008 |
| JP | 2011039028 A | 2/2011 |
| JP | 2016540221 A | 12/2016 |
| WO | 2013173524 A2 | 11/2013 |

OTHER PUBLICATIONS

International Search Report and Written Opinion issued by the European Patent Office acting as International Searching Authority in corresponding International Application No. PCT/US2019/026405 dated Jul. 18, 2019.
Australian Examination Report No. 1 issued in corresponding Appl. No. AU 2019245325 dated Nov. 16, 2020 (6 pages).
Office Action issued in corresponding JP Application No. 2020-552896, dated Nov. 30, 2021, pp. 1-8, together with English-language translation.
Office Action issued in corresponding CA Application No. 3,095,051 dated Jun. 2, 2022, pp. 1-5.
Office Action issued in corresponding CN Application No. 201980017943.6 dated Jul. 1, 2022, pp. 1-17.

* cited by examiner

POINT-OF-CARE DIAGNOSTIC SYSTEMS AND CONTAINERS FOR SAME

TECHNICAL FIELD

The present disclosure relates to medical diagnostics, and more particularly, to point-of-care medical diagnostic systems.

BACKGROUND

Medical guidance for many medical diagnostic systems, such as hematology analyzers, recommends analyzing a sample as soon as possible after drawing the sample. This recommendation can be difficult if the sample is obtained at the point of care but the test is to be performed at an external laboratory. Therefore, many doctors and veterinarians prefer to have point-of-care (POC) systems to analyze fresh samples.

POC medical diagnostic systems use various types of reagents and fluids to perform their analyses. Various types of packages exist for the reagents and fluids, and such packages must be delivered to and installed by the POC offices. Installations requiring a multitude of steps can confuse and frustrate operators. In some cases, POC diagnostic systems may still operate even if packages are improperly installed but may produce incorrect results. Accordingly, there is continuing interest in improving POC medical diagnostic systems and reagent and fluid packages for POC medical diagnostic systems.

SUMMARY

The present disclosure relates to point-of-care medical diagnostic systems and containers for such systems.

In accordance with aspects of the present disclosure, a medical diagnostic system includes a housing, a first receptacle in the housing for receiving a reagent container, a second receptacle in the housing for receiving a working fluid and waste container where the second receptacle is larger than the first receptacle, two reagent access needles positioned and fixed within the first receptacle with each of the two reagent access needles being substantially horizontal to horizontally access the reagent container, and a working fluid access needle and a waste access needle positioned and fixed within the second receptacle with the working fluid access needle and the waste access needle being substantially horizontal to horizontally access the working fluid and waste container.

In various embodiments, the first receptacle includes a top wall, a bottom wall, side walls, and a back wall. One of the two reagent access needles is positioned on the back wall adjacent to the bottom wall. The other of the two reagent access needles is positioned on the back wall adjacent to and above a center line between the top and bottom walls. In various embodiments, the reagent container and the first receptacle are shaped such that the reagent container must be inserted into the first receptacle in a particular orientation for the two reagent access needles to access the reagent container.

In various embodiments, the second receptacle includes a top wall, a bottom wall, side walls, and a back wall. The waste access needle is positioned on the back wall adjacent to the top wall. The working fluid access needle is positioned on the back wall adjacent to the bottom wall. In various embodiments, the working fluid and waste container and the second receptacle are shaped such that the working fluid and waste container must be inserted into the second receptacle in a particular orientation for the working fluid access needle and the waste access needle to access the working fluid and waste container. In various embodiments, a top portion of the second receptacle is narrower than a bottom portion of the second receptacle, and a top portion of the working fluid and waste container is narrower than a bottom portion of the working fluid and waste container.

In various embodiments, the medical diagnostic system includes a camera positioned such that it can view the first receptacle for imaging an encoded data-matrix code on the reagent container. In various embodiments, the medical diagnostic system uses the same camera positioned such that it can also view the second receptacle for imaging an encoded data-matrix code on the working fluid and waste container.

In various embodiments, the reagent container of the medical diagnostic system includes a top compartment and a bottom compartment that are fluidically separate. A septum between the top and bottom compartments connects them such that the top and bottom compartments are stationary relative to each other. The top compartment is defined by a housing having a top wall, a bottom wall, side walls, and an access opening positioned adjacent to the bottom wall of the top compartment. The bottom compartment is defined by a housing having a top wall, a bottom wall, side walls, and an access opening positioned adjacent to the bottom wall of the bottom compartment. In various embodiments, at least a portion of the bottom wall of the top compartment slopes downward toward the access opening of the top compartment. In various embodiments, the top wall of the bottom compartment is substantially parallel to the bottom wall of the top compartment. In various embodiments, a portion of the top wall of the bottom compartment is higher than a portion of the bottom wall of the top compartment.

In various embodiments, the working fluid and waste container of the medical diagnostic system includes a working fluid compartment having an access opening, a waste compartment having an access opening where the waste compartment is fluidically separate from the working fluid compartment, and a septum between and connecting the working fluid compartment and the waste compartment such that the working fluid compartment and the waste compartment are stationary relative to each other. In various embodiments, the second receptacle of the housing includes a top wall, a bottom wall, side walls, and a back wall. The access opening of the waste compartment is positioned adjacent to the top wall of the second receptacle, and the access opening of the working fluid compartment is positioned adjacent to the bottom wall of the second receptacle. In various embodiments, the waste compartment has an inner wall and an outer wall. The inner wall and the outer wall have a vertical cross-section in substantially a shape of a square with an open corner. The working fluid compartment has a first portion inward of the inner wall of the waste compartment and a second portion extending through the open corner where the second portion ends in the access opening of the working fluid compartment.

In accordance with aspects of the present disclosure, a container for a medical diagnostics system includes a top compartment defined by a housing having a top wall, a bottom wall, side walls, and an access opening positioned adjacent to the bottom wall of the top compartment, a bottom compartment defined by a housing having a top wall, a bottom wall, side walls, and an access opening positioned adjacent to the bottom wall of the bottom compartment, where the top compartment and the bottom compartment are fluidically separate, and a septum between and connecting the top and bottom compartments such that the top and bottom compartments are stationary relative to each other.

In various embodiments, at least a portion of the bottom wall of the top compartment slopes downward toward the access opening of the top compartment. In various embodiments, the top wall of the bottom compartment is substantially parallel to the bottom wall of the top compartment.

In accordance with aspects of the present disclosure, a container for a medical diagnostics system includes a waste compartment having an access opening, an inner wall, and an outer wall, where the inner wall and the outer wall have a vertical cross-section in substantially a shape of a square or rectangle with an open corner, a working fluid compartment having a first portion inward of the inner wall of the waste compartment and a second portion extending through the open corner, where the second portion ends in an access opening of the working fluid compartment and where the working fluid compartment is fluidically separate from the waste compartment, and a septum between and connecting the working fluid compartment and the waste compartment such that the working fluid compartment and the waste compartment are stationary relative to each other.

In various embodiments, the container is configured to fit into a receptacle having a top wall, a bottom wall, side walls, and a back wall, the access opening of the waste compartment is positioned adjacent to the top wall of the receptacle, and the access opening of the working fluid compartment is positioned adjacent to the bottom wall of the receptacle.

Further details and aspects of exemplary embodiments of the present disclosure are described in more detail below with reference to the appended figures.

DETAILED DESCRIPTION

Figure 1:
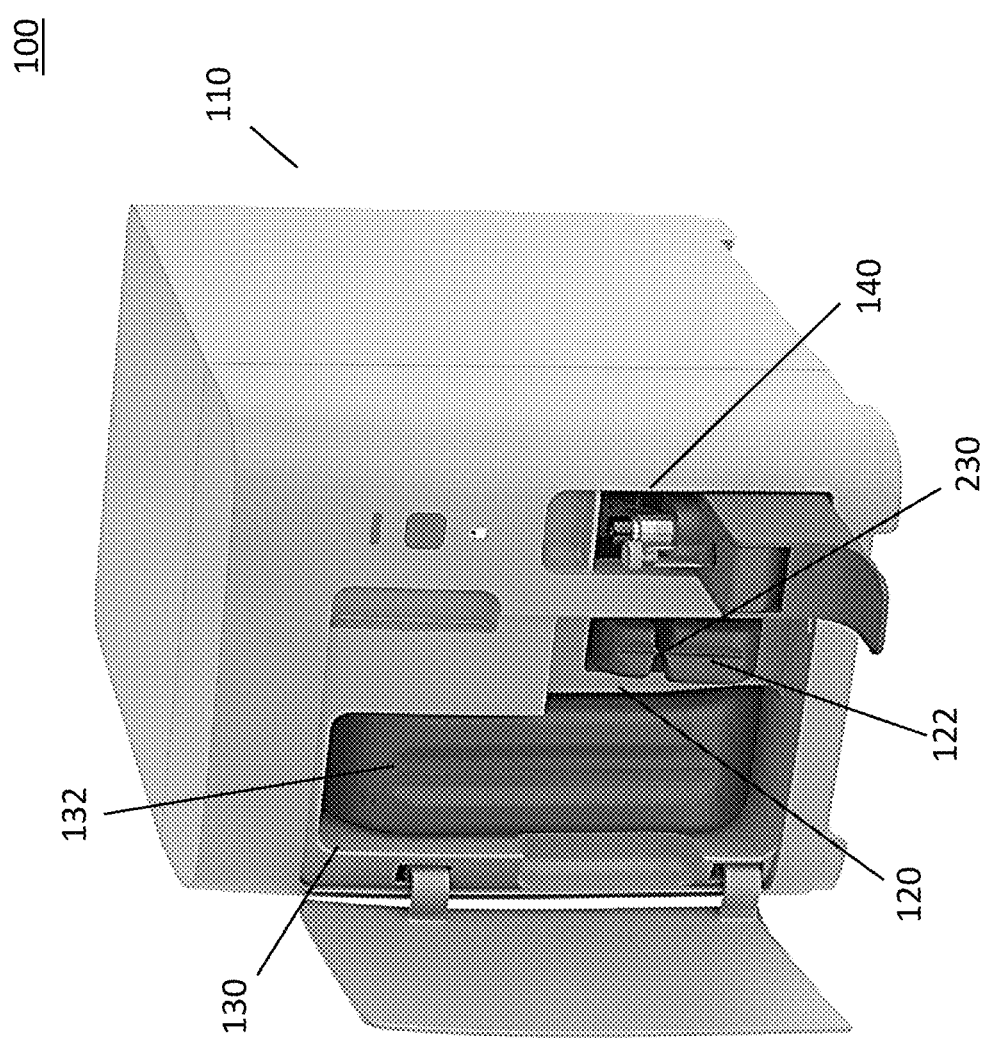
FIG. 1 is a diagram of an embodiment of a medical diagnostic system in accordance with aspects of the present disclosure.

The present disclosure relates to point-of-care medical diagnostic systems and containers for medical diagnostic systems. As used herein, point-of-care refers to a location where care is provided to human or animal patients, and a medical diagnostic system refers to a system that can analyze a sample obtained from a patient to diagnose a medical condition of the patient. Accordingly, a medical diagnostic system includes a patient sample analyzer, such as, but not limited to, a flow cytometer.

The following description will use flow-cytometry-based systems as an example of a medical diagnostic system. An example of a flow-cytometry-based analyzer is shown and described in U.S. Pat. No. 7,324,194, which is hereby incorporated by reference herein in its entirety, and which persons skilled in the art will understand. The present disclosure, however, is intended to and should be understood to apply to other types of medical diagnostic systems as well.

Flow cytometry systems include sub-systems such as fluidics, optics, and electronics sub-systems. A fluidics sub-system arranges a sample into a stream of particles, such as a stream of cells. The optics sub-system examines each cell by directed a laser beam to each cell and detecting scattered light using photo-detectors. Light is scattered according to size, complexity, granularity, and diameter of the cells, which form a "fingerprint" of each cell type. The electronics sub-system can process the fingerprints to classify, count, and/or otherwise analyze the cells/particles in the sample stream.

The fluidics sub-system has many responsibilities. For example, the fluidics sub-system uses a working fluid in various ways, including transporting dilutions (blood or quality control materials) to a laser for cell counting and morphology and/or to a hemoglobin module for hemoglobin measurement, acting as a sheath to carry blood cells sequentially past the laser, cleaning and/or priming the diagnostic system, and/or carrying waste to a waste container. The working fluid material is typically water-based and contains salt, surfactants, buffers and antimicrobials. The fluidic system is generally filled with this fluid at all times, except when a blood sample is being processed and moved through the system.

The fluidics sub-system also accesses reagents and applies them to the patient sample to produce desired reactions. For example, as persons skilled in the art will understand, reagents can be used to dye and distinguish particular cells, lyse red blood cells, and prepare cells for particular types of assays, among other things. In various embodiments, a red reagent is used to prepare a whole blood sample for evaluation primarily of red blood cells and platelets. The material is water-based and contains salt, surfactants, antimicrobials, and a stain (for reticulocytes). The red reagent is mixed in the proper dilution concentration with whole blood to cause the red blood cells to sphere and to stain the reticulocytes. The diluted sample is then transported to the flow cell for evaluation (counting and classification). In various embodiments, a white reagent is used to prepare a whole blood sample for evaluation of white blood cells. The material is water-based and contains salt, surfactants, and antimicrobials. The white reagent is mixed in the proper dilution concentration with whole blood to cause the red blood cells to lyse. The remaining white blood cells and platelets are left in the dilution and are transported to the flow cell for evaluation (counting and classification).

Accordingly, working fluid and reagents need to be installed and provided to the medical diagnostic system. Then, when the analysis is completed, waste fluids generated by the system need to be gathered and disposed in a safe manner. The following describe a medical diagnostic system and containers that address these concerns.

Referring now to FIG. 1, there is shown an exemplary medical diagnostic system 100. The illustrated medical diagnostic system 100 is configured and sized to reside within a point-of-care (POC) office. The illustrated system includes a housing 110 that forms the overall structure of the medical diagnostic system. The housing 110 includes a smaller receptacle 120 that is intended to receive a reagent container 122 and a larger receptacle 130 that is intended to receive a working fluid and waste container 132. The reagent container 122 stores reagents that will be used by the diagnostic system 100, and the working fluid and waste container 132 operates to provide working fluid to the diagnostic system 100 and to receive waste fluid from the diagnostic system 100. At the right side of the housing 110, another receptacle 140 can receive various fluids and materials, including a patient sample, system cleaning fluid, and quality control materials, among other things.

As will be described in more detail below, the receptacles 120, 130 and the containers 122, 132 are configured so that an operator can slide a container 122, 132 horizontally into a receptacle. In accordance with one aspect of the present disclosure, the interior of the receptacles 120, 130 include fluid access needles (not shown) that are oriented horizontally. As the containers 122, 132 slide horizontally into the receptacles 120, 130, the horizontal needles engage access openings in the containers. In various embodiments, the access needles are substantially horizontal in that the needles are intended to be horizontal but may not be fully horizontal due to, for example, slight manufacturing imperfections or limitations, or slight loosening of the needles within the receptacle over time due to wear, or other material, manufacturing, or environmental imperfections.

Figure 2:
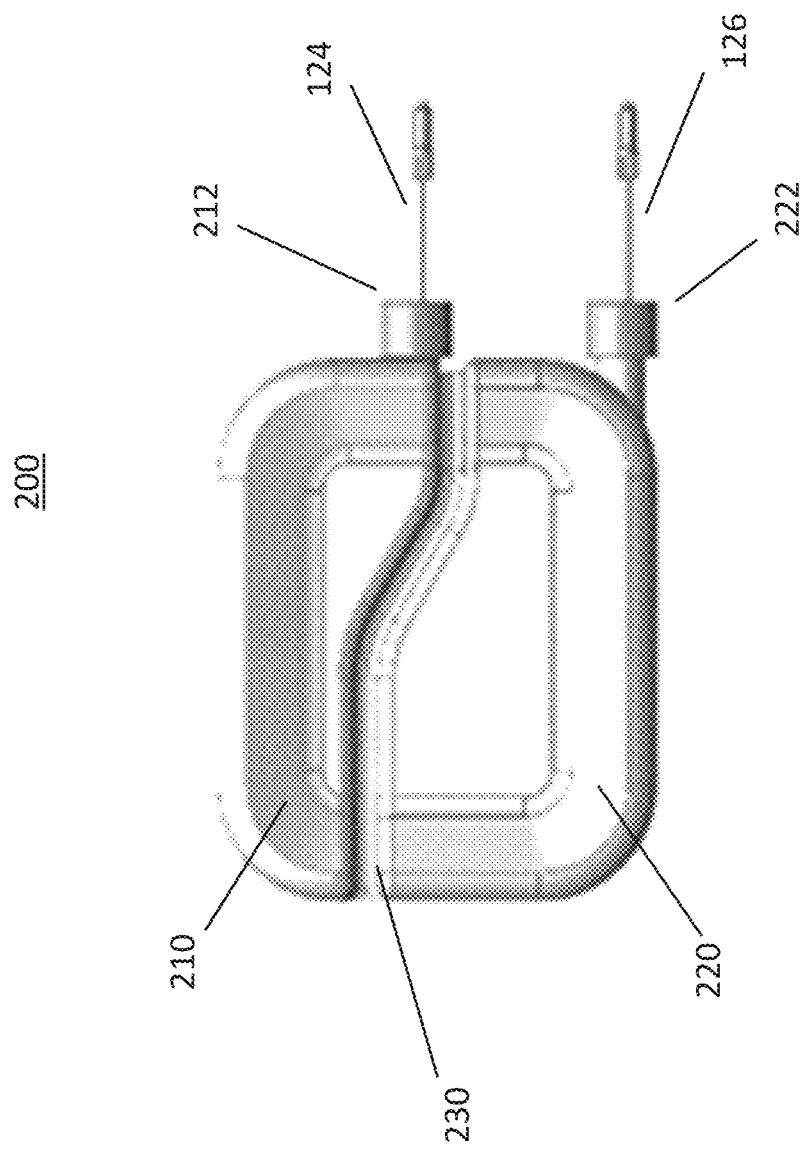
FIG. 2 is a diagram of an embodiment of a reagent container, in accordance with aspects of the present disclosure.

Referring now to FIG. 2, there is shown a side view of an exemplary reagent container 200. The reagent container includes a top compartment 210 and a bottom compartment 220. The two compartments 210, 220 are fluidically separate. A septum 230 between the top and bottom compartments 210, 220 connects the two compartments and hold them stationary relative to each other. In various embodiments, the reagent container is a single molded vessel, where the two compartments and the septum between the two compartments are formed in the same molding process. The top compartment 210 and the bottom compartment 220 both end with an access opening 212, 222. The access openings 212, 222 are positioned so that the reagent access needles 124, 126 located within the smaller receptacle 130 of the diagnostic system can access them. In various embodiments, the access openings can be covered by a fluid seal that prevents the reagents from spilling. The reagent access needles 124, 126 can puncture the fluid seal to access the reagents. The reagent access needles 124, 126 are illustrated for clarity and are not a part of the reagent container.

Figure 3:
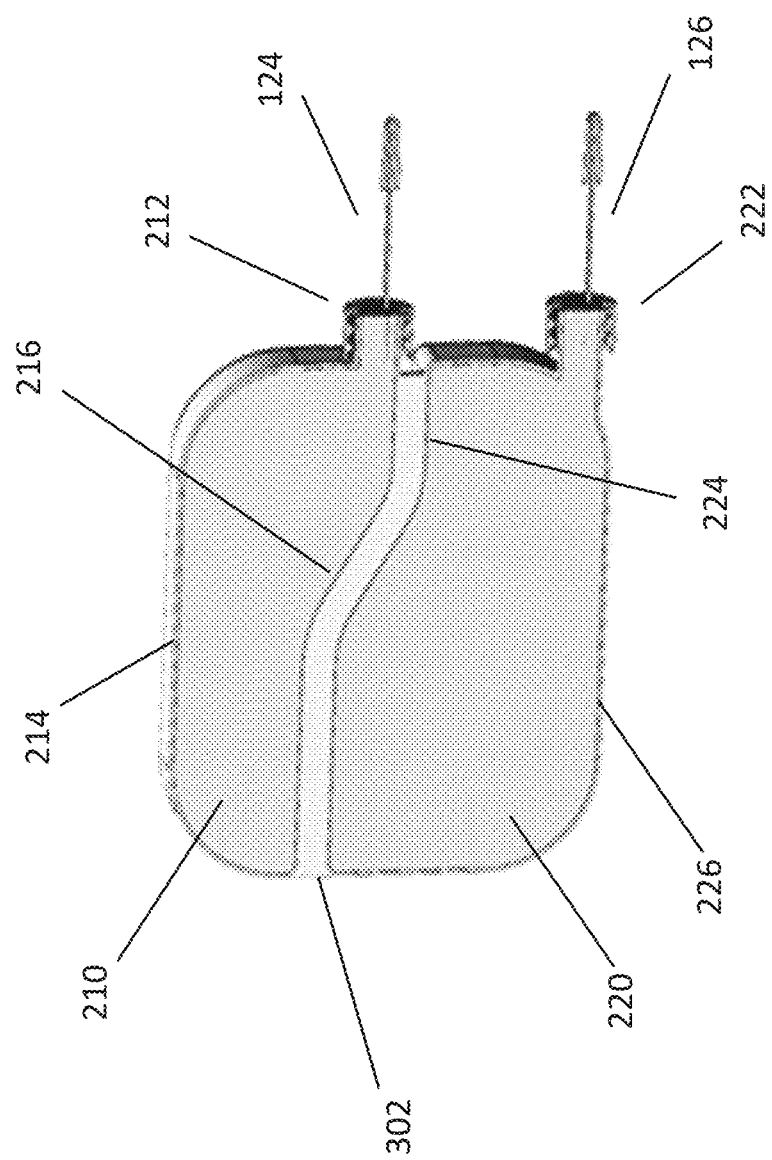
FIG. 3 is a diagram of a cross-section of the reagent container of FIG. 2, in accordance with aspects of the present disclosure.

FIG. 3 shows a vertical cross-section of the reagent container 200 of FIG. 2. The top compartment 210 includes a top wall 214 and a bottom wall 216, and the bottom compartment 220 includes a top wall 224 and a bottom wall 226. Side walls of the top and bottom compartments 210, 220 are illustrated in FIG. 2. Depending on the location of the vertical cross-section, the area 302 between the top compartment 210 and the bottom compartment 220 may be the septum 230 or may be empty space. For example, as shown in FIG. 1, the septum 230 is narrower than the widths of the top and bottom compartments 210, 220. If the vertical cross-section is taken over the septum 230, then the septum 230 will be in the area 302 between the top and bottom compartments. If the vertical cross-section is taken outside of the septum 230, then the area 302 between the top and bottom compartments 210, 220 will be air. In various embodiments, the septum 230 can be wider or narrower or another width than as illustrated in FIG. 1.

As shown in FIG. 3, the access openings 212, 222 of the top and bottom compartments 210, 220 are adjacent to the bottom walls 216, 226. The reagent access needles 124, 126 are positioned to insert into the bottom portion of the access openings 212, 222, so as to reach as much of the reagents as possible. A portion of the bottom wall 216 of the top compartment 210 slopes downward towards the access opening 212 of the top compartment. Thus, essentially all of the reagent in the top compartment 210 will be able to reach the access opening 212 and be accessed by the fluid access needle 124. In contrast, in the illustrated embodiment, the bottom compartment 220 does not include a slope at its bottom wall 226. Thus, some portion of the reagent in the bottom compartment 220 will be inaccessible to the fluid access needle 126. In various embodiments, the bottom wall 226 of the bottom compartment 220 can include a downward slope.

The particular shapes and relative sizes of the compartments are exemplary, and other variations and configurations are contemplated. For example, in the embodiment of FIGS. 2 and 3, the top compartment 210 is smaller than the bottom compartment 220. For example, the top compartment 210 may hold from about 60 mL to about 130 mL, from about 70 mL to about 120 mL, from about 80 mL to about 110 mL, from about 90 mL to about 100 mL, or, most preferably, about 95 mL of reagent; and the bottom compartment 220 may hold from about 175 mL to about 100 mL, from about 165 mL to about 110 mL, from about 155 mL to about 120 mL, from about 145 mL to about 130 mL, or, most preferably, about 139 mL of reagent. In various other embodiments, other capacities are contemplated, and other proportions of capacities between the top and bottom compartments 210, 220 are contemplated.

Figure 4:
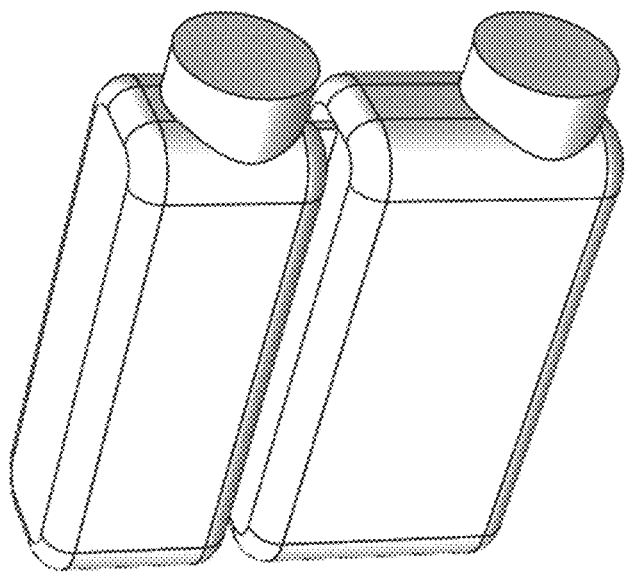
FIG. 4 is a diagram of another embodiment of a reagent container, in accordance with aspects of the present disclosure.

In the illustrated embodiment, the bottom wall 216 of the top compartment 210 and the top wall 224 of the bottom compartment 220 are parallel or substantially parallel. They may be substantially parallel even when they are intended to be entirely parallel because of, for example, manufacturing imperfections. In various other embodiments, the bottom wall 216 of the top compartment 210 and the top wall 224 of the bottom compartment 220 can be intentionally non-parallel. Additionally, in the illustrated embodiment, a portion of the top wall 224 of the bottom compartment 220 is higher than a portion of the bottom wall 216 of the top compartment 210 because of the downward slope in those walls. In various other embodiments, there may be no downward slope in those walls, such as in the example of FIG. 4.

In the illustrated embodiment, the septum 230 adjacent to the access openings 212, 222 is located about halfway between the top wall 214 of the top compartment 210 and the bottom wall 226 of the bottom compartment 220. Thus, the access opening 212 of the top compartment 210 is located adjacent to and above this center line. The reagent access needles 124, 126 are located in corresponding positions. The smaller receptacle 120 of the diagnostic system includes a top wall, a bottom wall, a back wall, and side walls (not shown). One reagent access needle 126 is positioned on the back wall adjacent to the bottom wall of the smaller receptacle 120, and the other reagent access needle 124 is positioned on the back wall adjacent to and above the center line between the top and bottom walls of the smaller receptacle 120 (not shown). Thus, the reagent access needles 124, 126 can access the compartments 210, 220 only when the reagent container 200 is inserted into the smaller receptacle 120 in a particular orientation. In various other embodiments, the locations of the access openings 212, 222 and the reagent access needles 124, 126 can be in other positions, as shown for example, in FIG. 4.

Described above herein are aspects of the medical diagnostic system and the reagent container. The following will describe aspects of the working fluid and waste container. As shown in FIG. 1, the working fluid and waste container 132 is larger than the reagent container 122. In various embodiments, other size proportions between the reagent container 122 and the working fluid and waste container 132 are contemplated.

Figure 5:
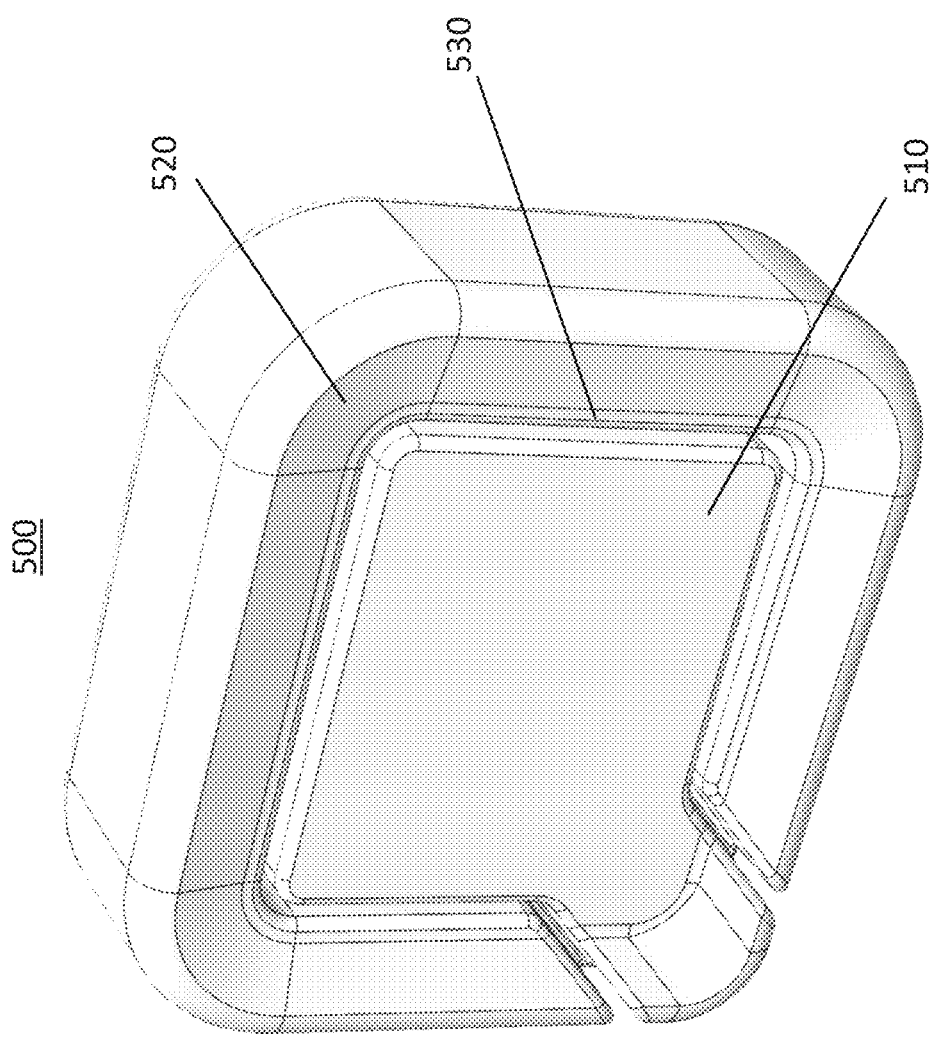
FIG. 5 is a diagram of an embodiment of a working fluid and waste container, in accordance with aspects of the present disclosure.
Figure 6:
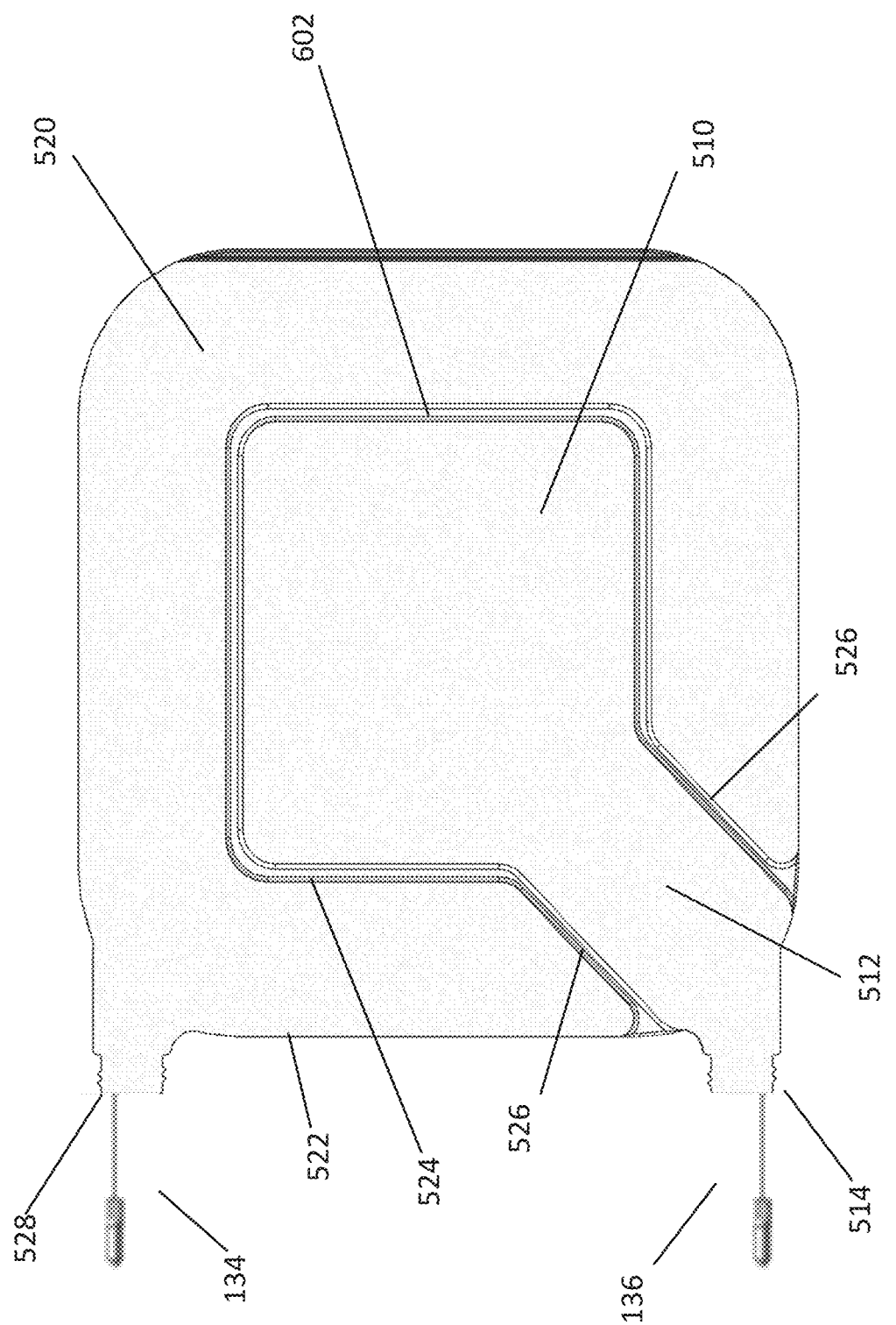
FIG. 6 is a diagram of a cross-section of the working fluid and waste container of FIG. 5, in accordance with aspects of the present disclosure.

Referring to FIG. 5, there is shown an embodiment of a working fluid and waste container 500 that includes a working fluid compartment 510 and a waste compartment 520. The working fluid and waste compartments 510, 520 are fluidically separate. A septum 530 is positioned between the compartments and connects them such that the working fluid and waste compartments 510, 520 are stationary relative to each other. In various embodiments, the working fluid and waste container is a single molded vessel, where the two compartments and the septum between the two compartments are formed in the same molding process. Referring also to FIG. 6, a vertical cross-section of the working fluid and waste container 500 of FIG. 5 is shown. Depending on the location of the vertical cross-section, the area 602 between the waste compartment 520 and the working fluid compartment 510 may be the septum 530 or may be empty space. For example, as shown in FIG. 5, the septum 530 is narrower than the widths of the working fluid and waste compartments 510, 520. If the vertical cross-section is taken over the septum 530, then the septum 530 will be in the area 602 between the working fluid and waste compartments 510, 520. If the vertical cross-section is taken outside of the septum 530, then the area 602 between the working fluid and waste compartments 510, 520 will be air. In various embodiments, the septum 530 can be wider or narrower or another width than as illustrated in FIG. 5.

With continuing reference to FIG. 6, the waste compartment 520 has an outer wall 522, an inner wall 524, and end walls 526 connecting the outer and inner walls 522, 524. The outer wall 522 and the inner wall 524 have vertical cross-sections that are substantially in the shape of a square or rectangle with an open corner. The cross-sections may have substantially a particular shape, but not exactly a particular shape, because of, for example, rounded corners or manufacturing imperfections or material stress over time. The working fluid compartment 510 includes a portion that is within the inner wall 524 of the waste compartment 520 and another portion 512 that extends through the open corner of the waste compartment 520 and ends at an access opening 512.

With reference to the medical diagnostic system of FIG. 1, the working fluid and waste container 132 slides into the larger receptacle 130. The larger receptacle 130 includes a top wall, a bottom wall, a back wall, and side walls (not shown). With reference to the larger receptacle 130, the access opening 528 of the waste compartment 520 is positioned adjacent to the top wall of the larger receptacle 130, and the access opening 514 of the working fluid compartment 510 is positioned adjacent to the bottom wall of the second receptacle 130. The working fluid and waste access needles 134, 136 are located in corresponding positions. The waste access needle 134 is positioned on the back wall of the larger receptacle 130 adjacent to the top wall of the larger receptacle 130, and the working fluid access needle 136 is positioned on the back wall of the larger receptacle 130 adjacent to the bottom wall of the larger receptacle 130. In various embodiments, the working fluid access needle 136 is positioned towards the bottom portion of the access opening 514 for the working fluid compartment 510. In this manner, substantially all of the working fluid is accessible to the working fluid access needle 136. In various embodiments, the waste access needle 134 is positioned towards the top portion of the access opening 518 for the waste compartment 520. In this manner, the waste compartment 520 can be filled without the stale waste fluid in the waste compartment 520 contacting the waste access needle 134, thereby providing less risk of contaminating the waste access needle 134 or of backflow through the waste access needle 134. In various embodiments, the access openings 514, 528 can be covered by a fluid seal that prevents the fluid from spilling. The working fluid and waste access needles 134, 136 can puncture the fluid seal to access the interior of the compartments 510, 520.

Referring again to FIG. 1, in accordance with aspects of the present disclosure, the working fluid and waste container 132 and the larger receptacle 130 are shaped such that the working fluid and waste container 132 must be inserted into the larger receptacle 130 in a particular orientation for the working fluid access needle 136 and the waste access needle 134 to access the working fluid and waste container 132. In various embodiments, the top portion of the larger receptacle 130 is narrower than the bottom portion of the larger receptacle 130, and the top portion of the working fluid and waste container 132 is also narrower than the bottom portion of the working fluid and waste container 132. Thus, the working fluid and waste container 132 must be inserted in the correct orientation for the working fluid access needle 136 and the waste access needle 134 to access the access openings of the working fluid and waste container 130.

The working fluid and waste container of FIGS. 5 and 6 is exemplary, and other shapes and configurations are contemplated to be within the scope of the present disclosure. For example, other embodiments of the working fluid and waste container are shown in FIGS. 7-10.

Figure 7:
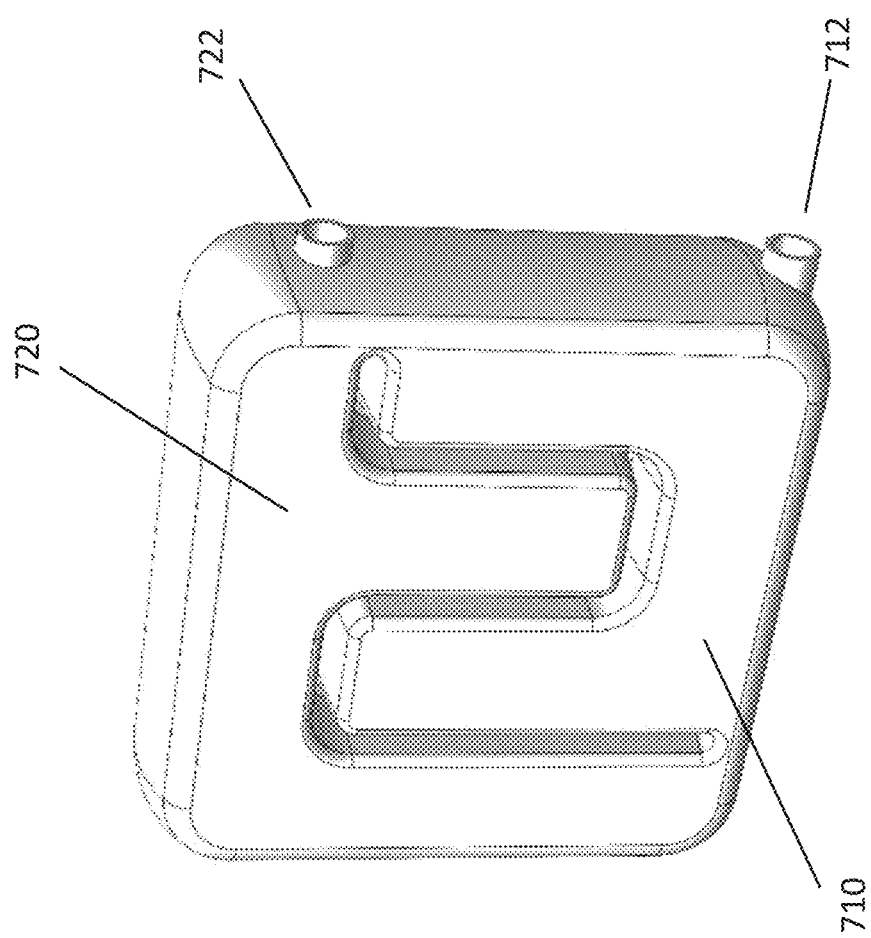
FIG. 7 is a diagram of another embodiment of a working fluid and waste container, in accordance with aspects of the present disclosure.

In the embodiment of FIG. 7, the working fluid compartment 710 has a substantially U-shape. The waste compartment 720 inter-locks with the working fluid compartment and has a portion above the working fluid compartment, a portion within the U-shape of the working fluid compartment, and a portion outside of and adjacent to the working fluid compartment. The working fluid compartment 710 and the waste compartment 720 are fluidically separate, and a septum connects between the compartment such that the working fluid compartment 710 and the waste compartment 720 are stationary relative to each other. The access opening 722 of the waste compartment 720 is adjacent to the top of the container, and the access opening 712 of the working fluid compartment 710 is adjacent to the bottom of the container.

Figure 8:
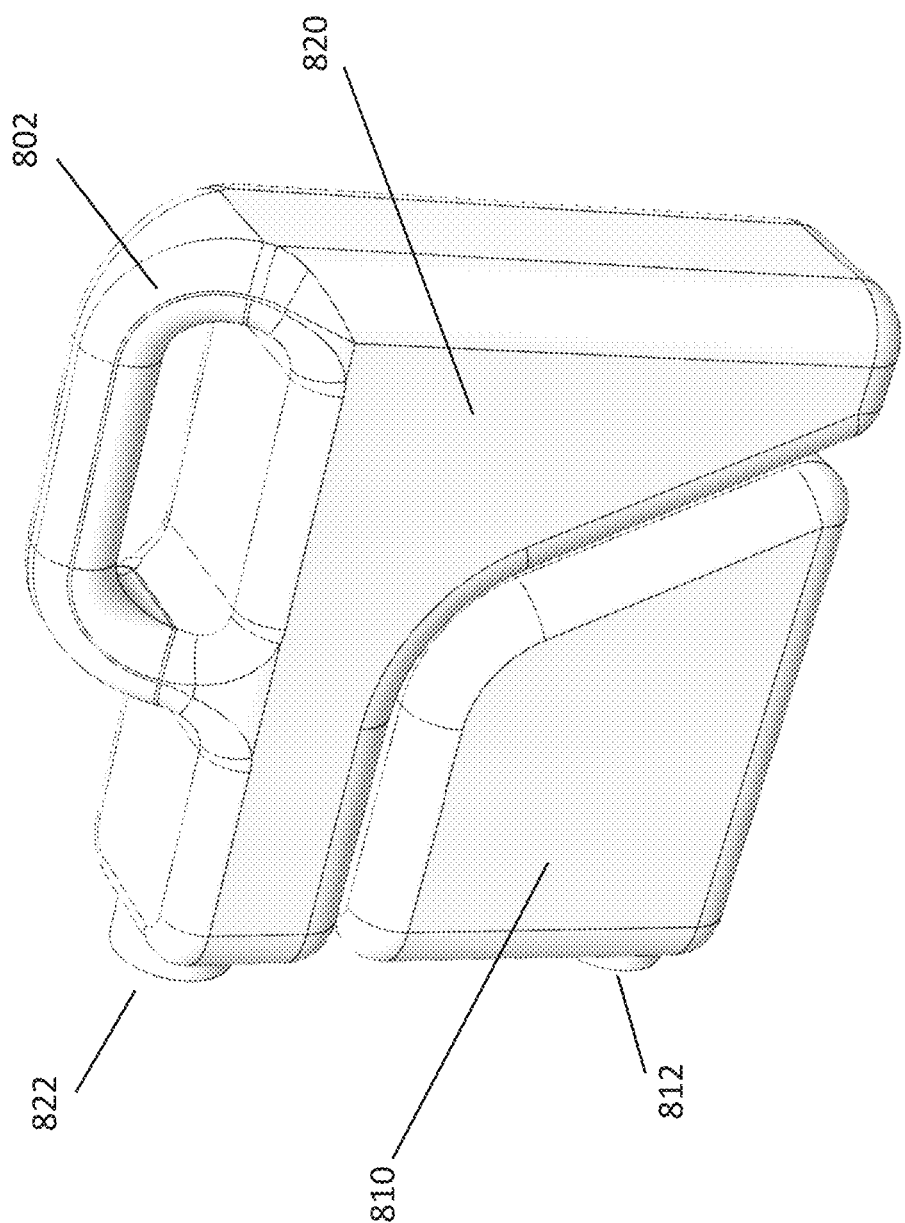
FIG. 8 is a diagram of yet another embodiment of a working fluid and waste container, in accordance with aspects of the present disclosure.

In the embodiment of FIG. 8, the working fluid and waste container includes a handle 802 at the top of the container. The handle 802 enables an operator to more easily carry the container when it is outside the medical diagnostic system. A handle 802 as shown in FIG. 8 can be applied to any other embodiment disclosed herein or any embodiment contemplated to be within the scope of the present disclosure. With continuing reference to FIG. 8, the working fluid compartment 810 is substantially in the shape of a trapezoid, and the waste compartment 820 has a complementary shape such that the overall shape of working fluid and waste container is square or rectangular, when not considering the shape of the handle 802. The working fluid compartment 810 and the waste compartment 820 are fluidically separate, and a septum connects between the compartment such that the working fluid compartment 810 and the waste compartment 820 are stationary relative to each other. The access opening 822 of the waste compartment 820 is adjacent to the top of the container, and the access opening 812 of the working fluid compartment 810 is adjacent to the bottom of the container.

Figure 9:
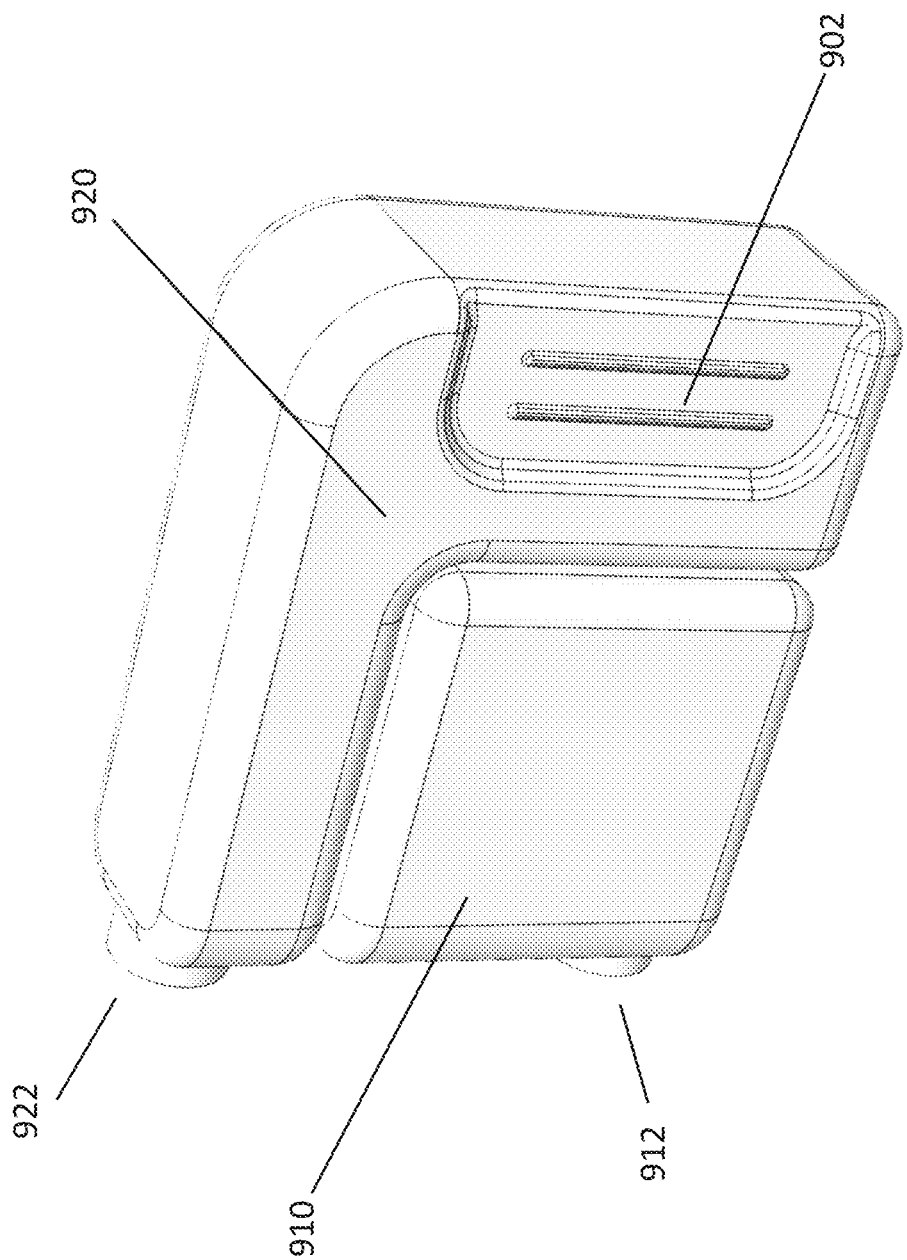
FIG. 9 is a diagram of still another embodiment of a working fluid and waste container, in accordance with aspects of the present disclosure.

In the embodiment of FIG. 9, the working fluid and waste container includes a grip-enhancement 902. The grip-enhancement 902 enables an operator to more easily handle the container when inserting the container into the medical diagnostics system or removing the container. A grip enhancement 902 as shown in FIG. 9 can be applied to any other embodiment disclosed herein or any embodiment contemplated to be within the scope of the present disclosure. With continuing reference to FIG. 9, the working fluid compartment 910 is substantially in the shape of a square, and the waste compartment 920 has a complementary shape such that the overall shape of working fluid and waste container is square or rectangular. The working fluid compartment 910 and the waste compartment 920 are fluidically separate, and a septum connects between the compartments such that the working fluid compartment 910 and the waste compartment 920 are stationary relative to each other. The access opening 922 of the waste compartment 920 is adjacent to the top of the container, and the access opening 912 of the working fluid compartment 910 is adjacent to the bottom of the container.

Figure 10:
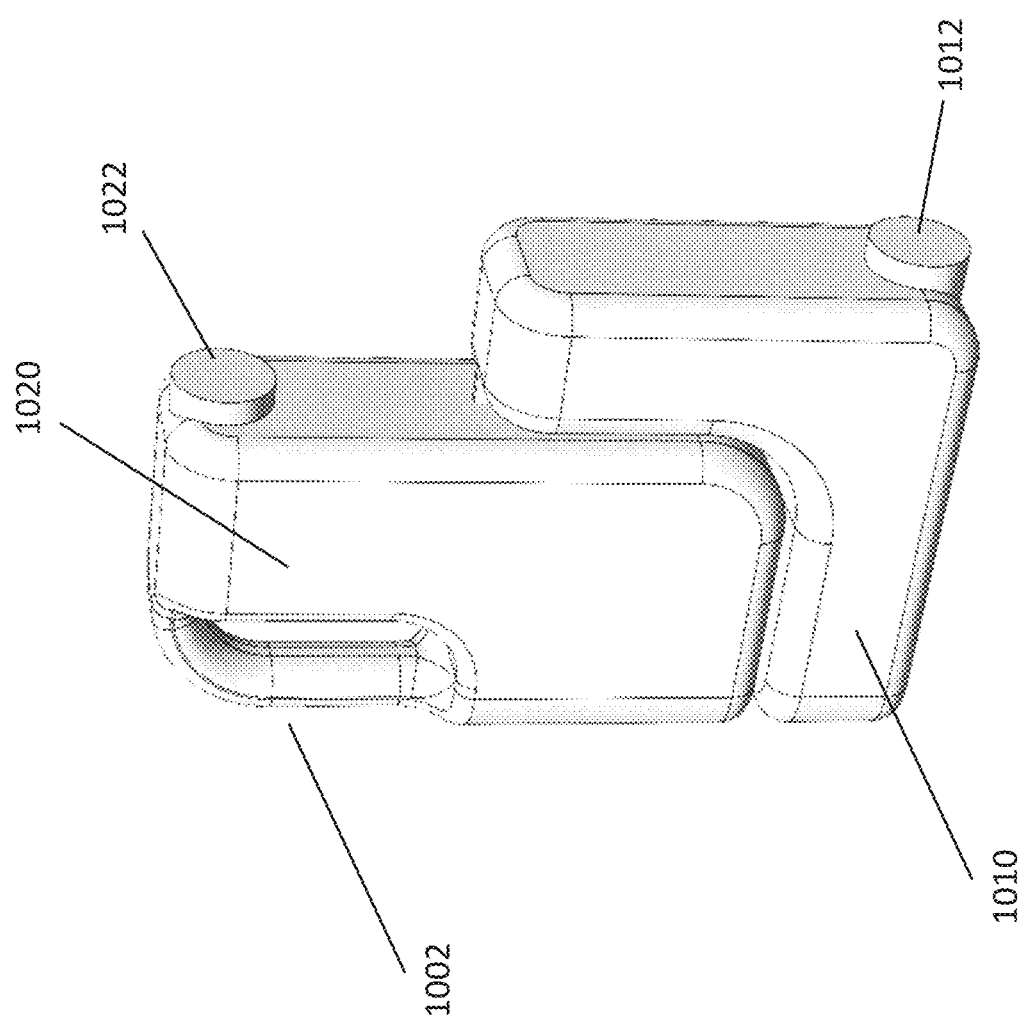
FIG. 10 is a diagram of another embodiment of a working fluid and waste container, in accordance with aspects of the present disclosure.

In the embodiment of FIG. 10, the working fluid and waste container includes a handle 1002 at a corner of the container. A handle 1002 as shown in FIG. 10 can be applied to any other embodiment disclosed herein or any embodiment contemplated to be within the scope of the present disclosure. With continuing reference to FIG. 10, the working fluid compartment 1010 has substantially an L-shape, and the waste compartment 1020 has a substantially rectangular shape, when not considering the shape of the handle 1002. The working fluid compartment 1010 and the waste compartment 1020 are fluidically separate, and a septum connects between the compartments such that the working fluid compartment 1010 and the waste compartment 1020 are stationary relative to each other. The access opening 1022 of the waste compartment 1020 is adjacent to the top of the container, and the access opening 1012 of the working fluid compartment 1010 is adjacent to the bottom of the container.

Figure 11:
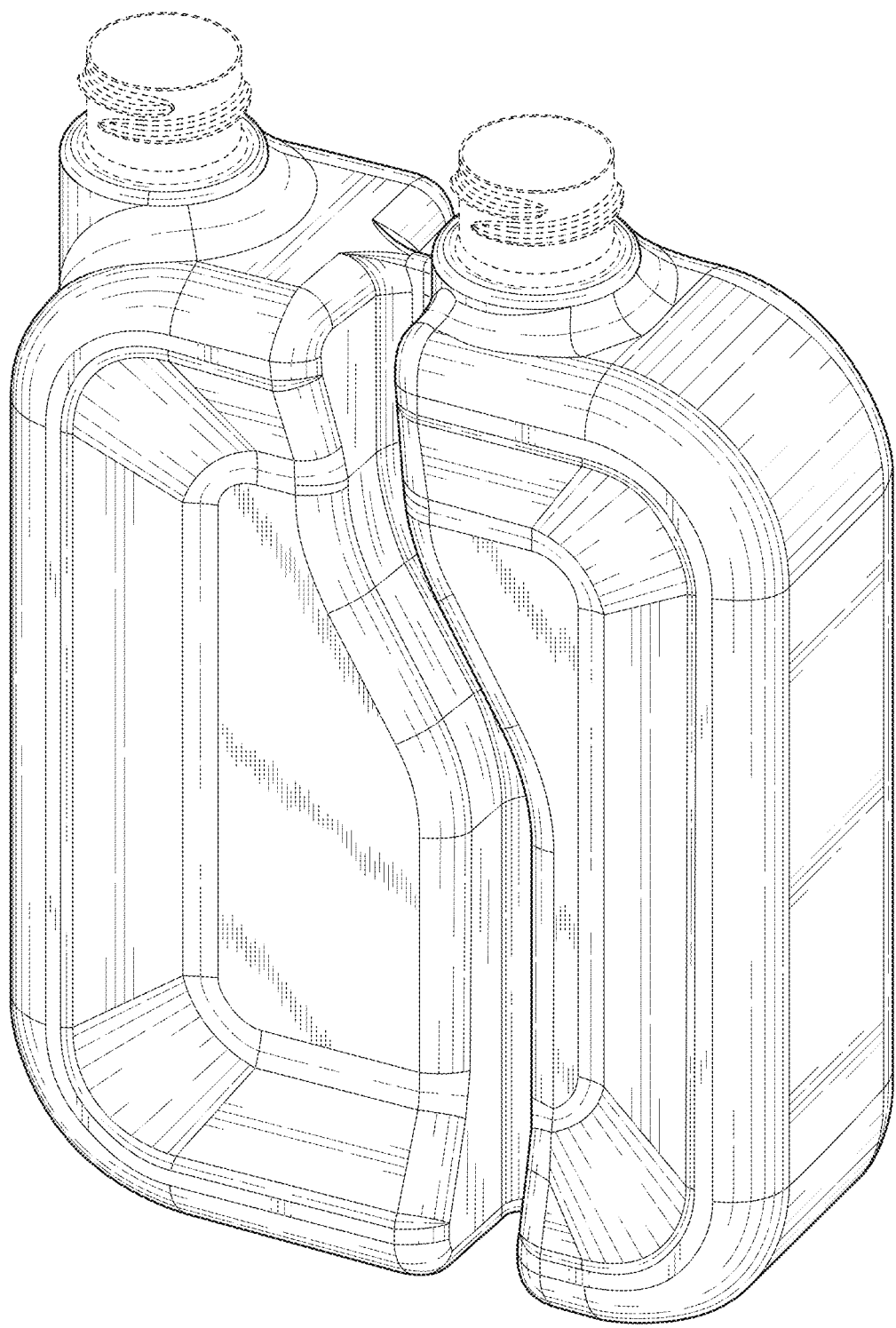
FIG. 11 is a perspective view of the reagent container of FIG. 2 with contour lines that more clearly show the shape of the container, in accordance with aspects of the present disclosure.
Figure 12:
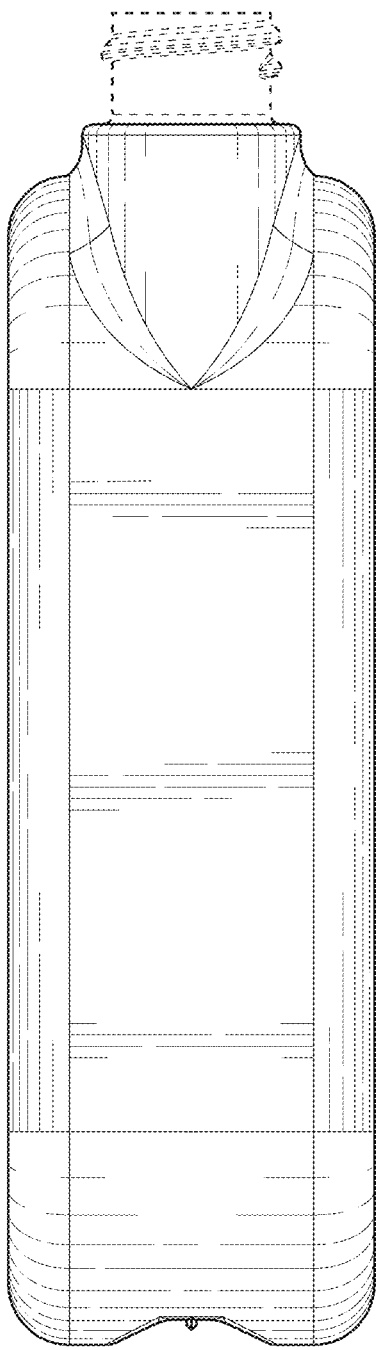
FIG. 12 is a bottom plan view of the reagent container of FIG. 2, in accordance with aspects of the present disclosure.
Figure 13:
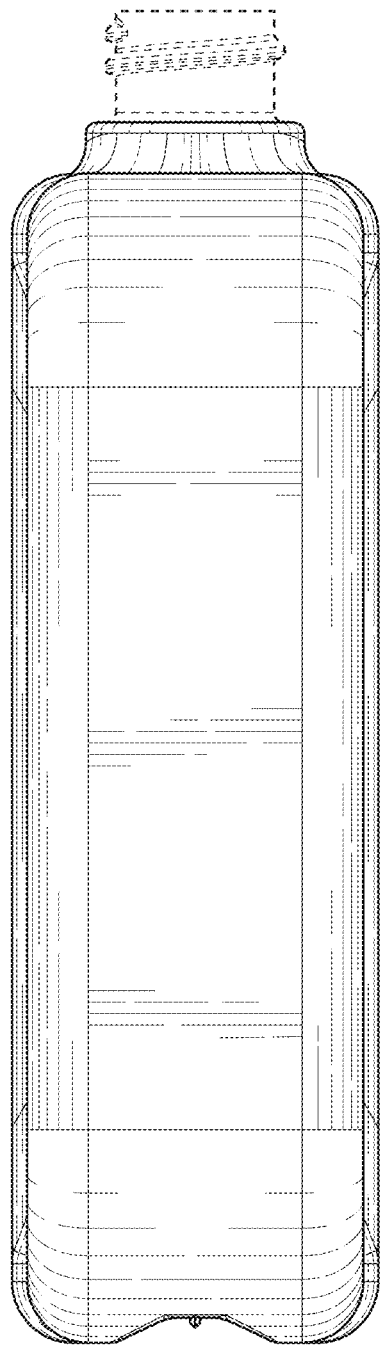
FIG. 13 is a top plan view of the reagent container of FIG. 2, in accordance with aspects of the present disclosure.
Figure 14:
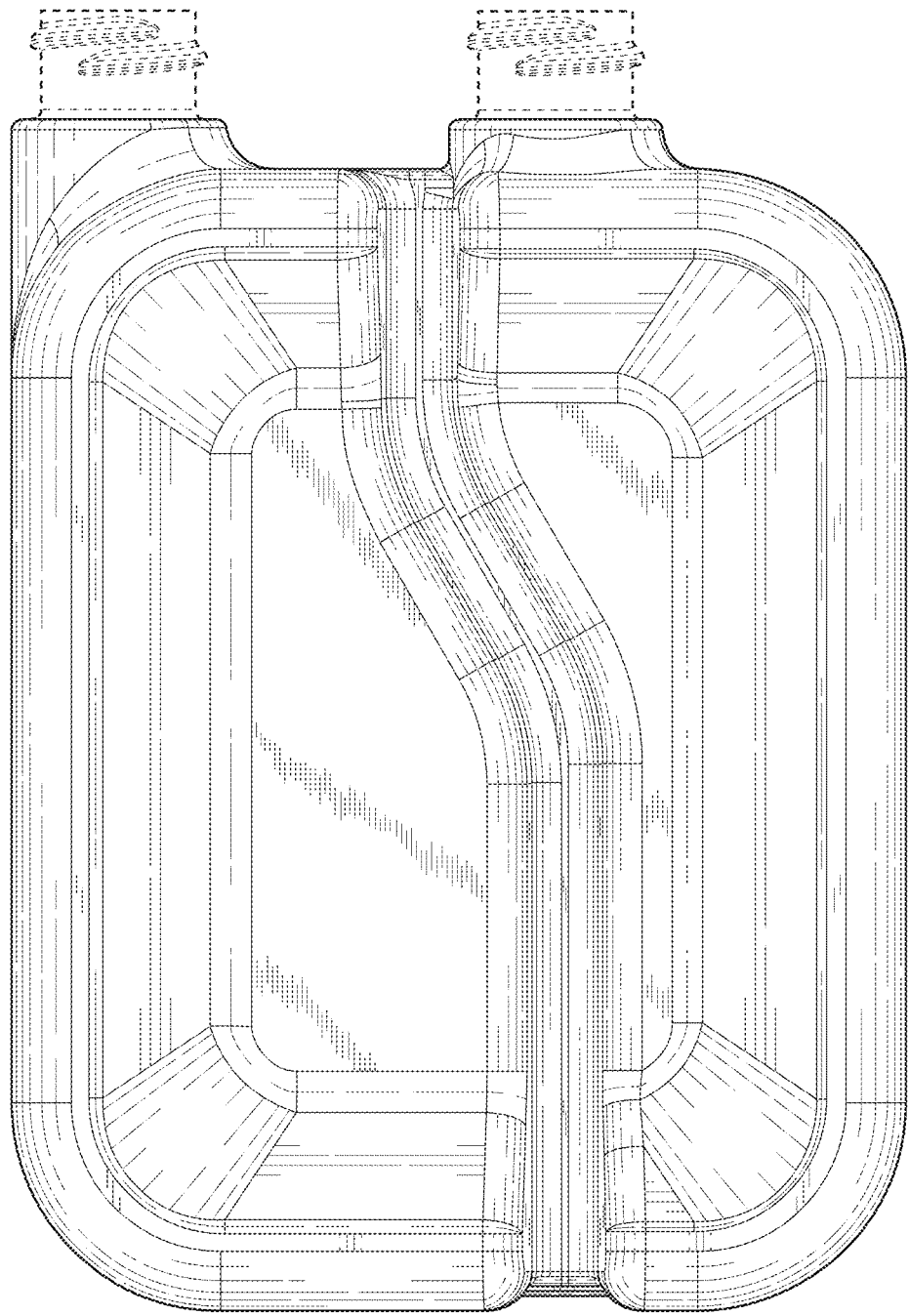
FIG. 14 is a left side elevational view of the reagent container of FIG. 2, in accordance with aspects of the present disclosure.
Figure 15:
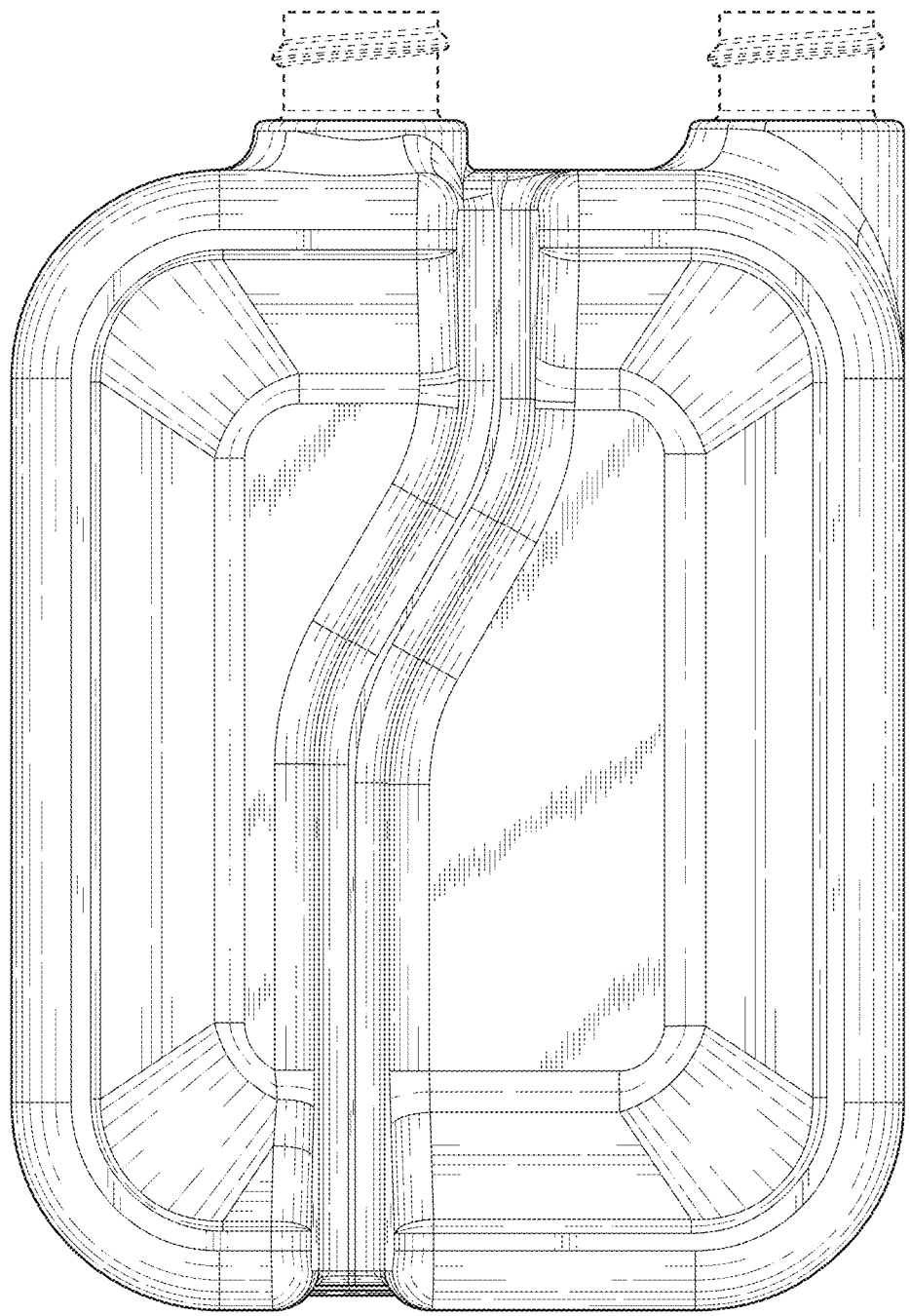
FIG. 15 is a right side elevational view of the reagent container of FIG. 2, in accordance with aspects of the present disclosure.
Figure 16:
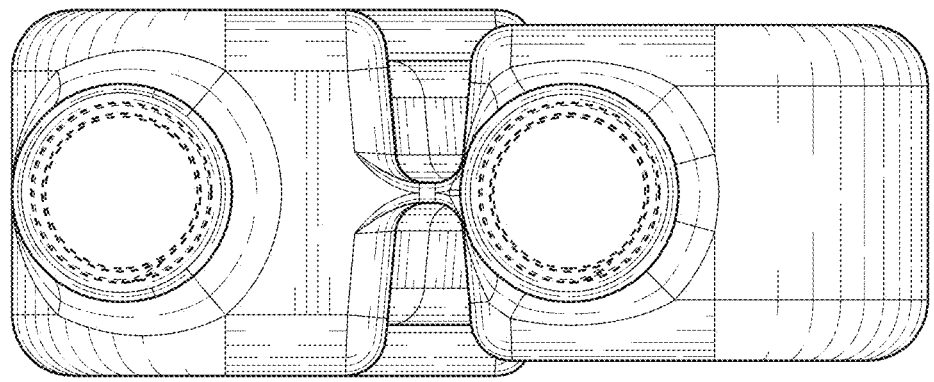
FIG. 16 is a front elevational view of the reagent container of FIG. 2, in accordance with aspects of the present disclosure.
Figure 17:
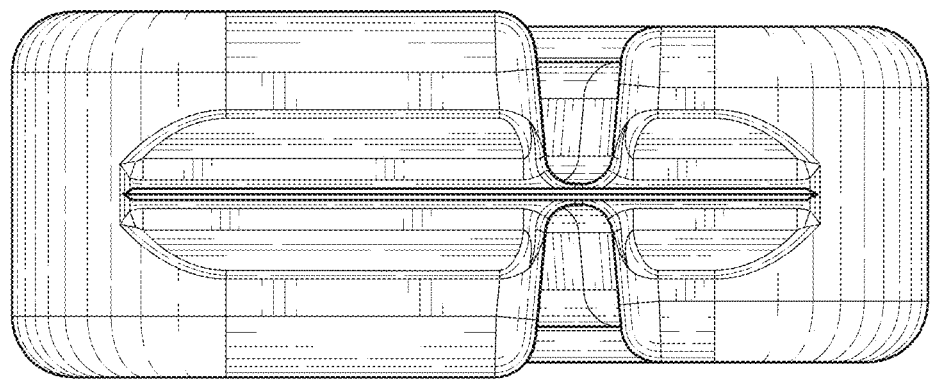
FIG. 17 is a rear elevational view of the reagent container of FIG. 2, in accordance with aspects of the present disclosure.
Figure 18:
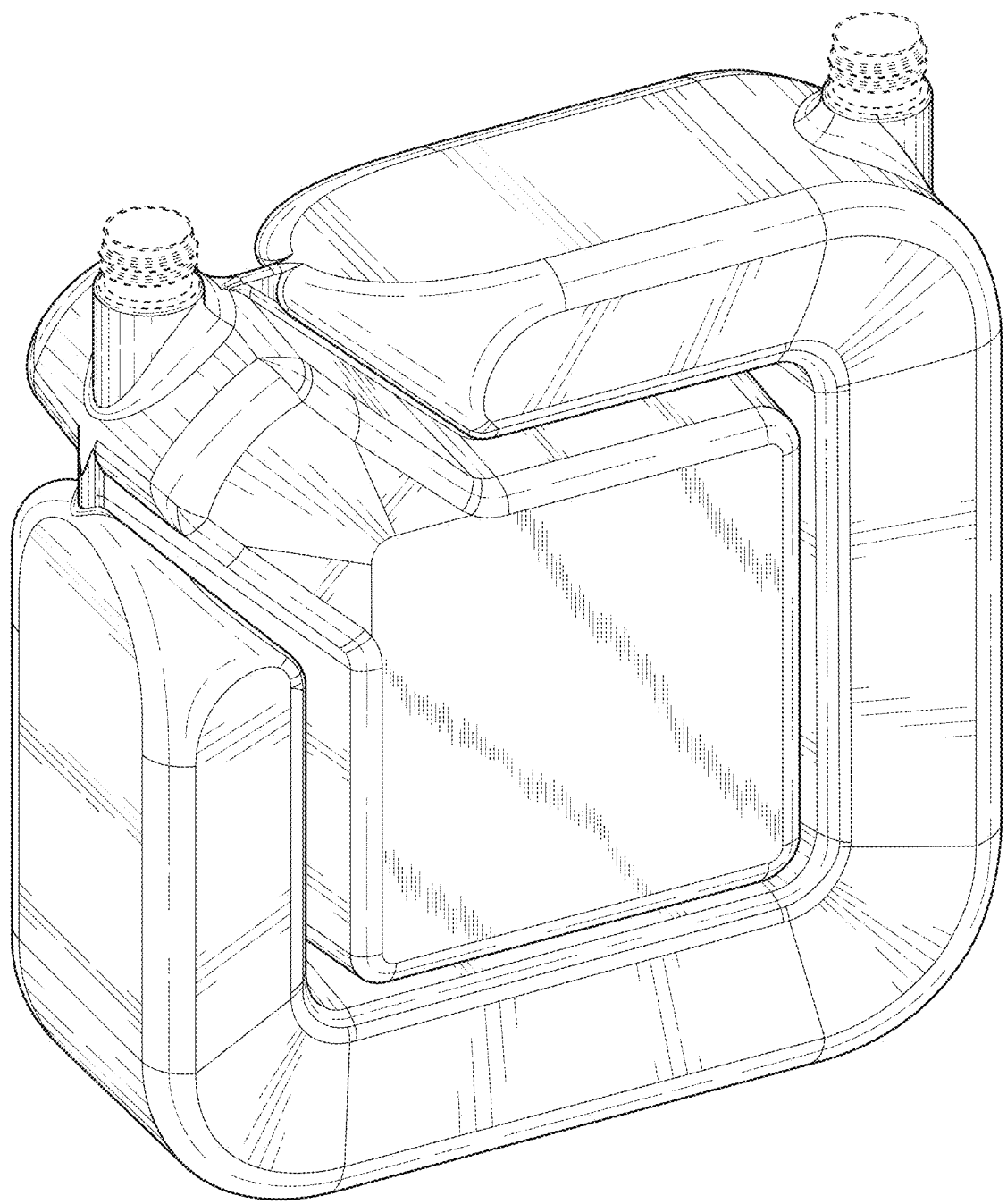
FIG. 18 is a perspective view of the working fluid and waste container of FIG. 5 with contour lines that more clearly show the shape of the container, in accordance with aspects of the present disclosure.
Figure 19:
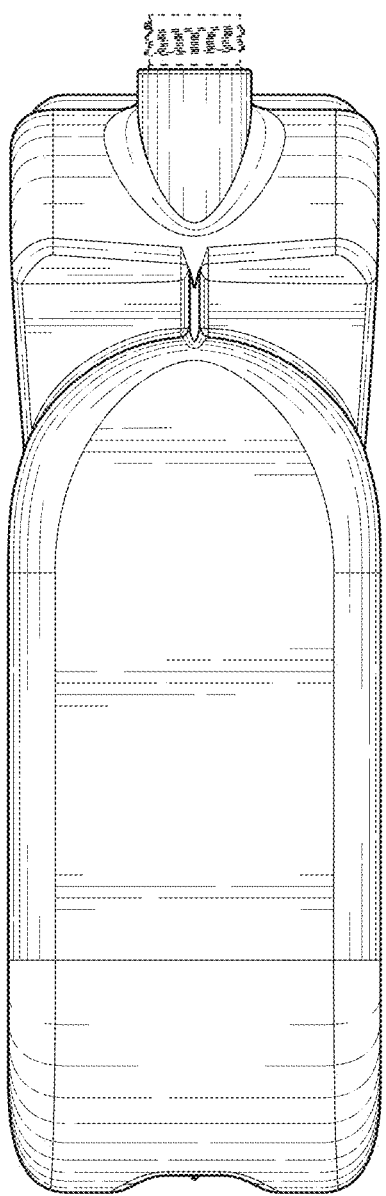
FIG. 19 is a bottom plan view of the working fluid and waste container of FIG. 5, in accordance with aspects of the present disclosure.
Figure 20:
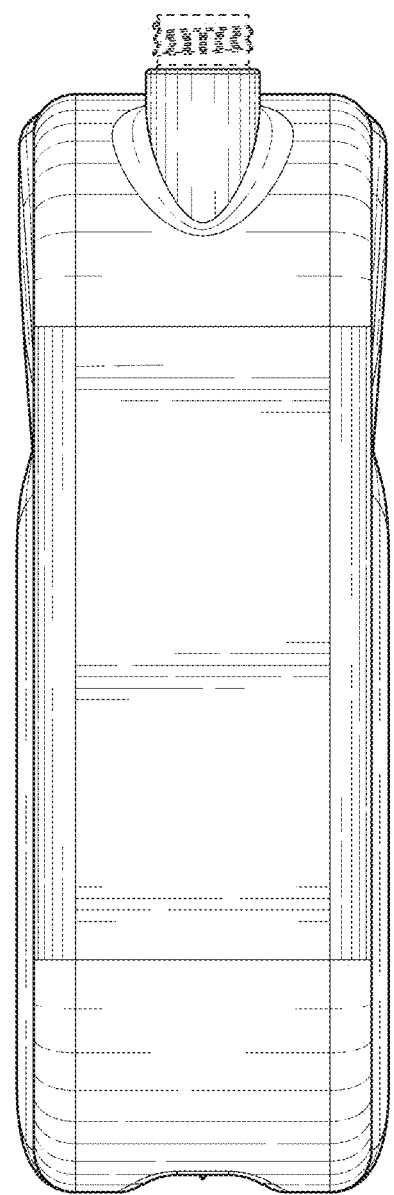
FIG. 20 is a top plan view of the working fluid and waste container of FIG. 5, in accordance with aspects of the present disclosure.
Figure 21:
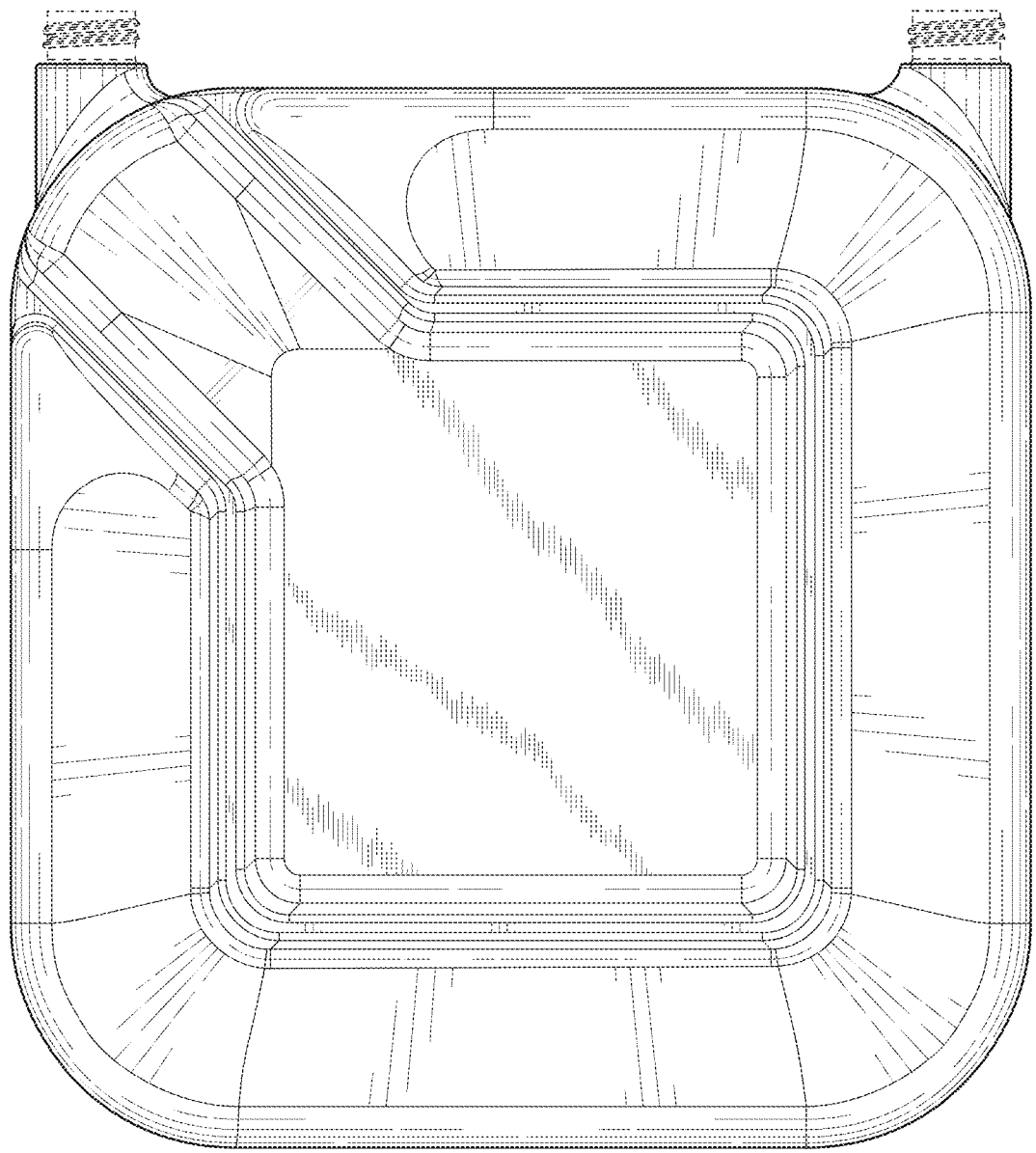
FIG. 21 is a left side elevational view of the working fluid and waste container of FIG. 5, in accordance with aspects of the present disclosure.
Figure 22:
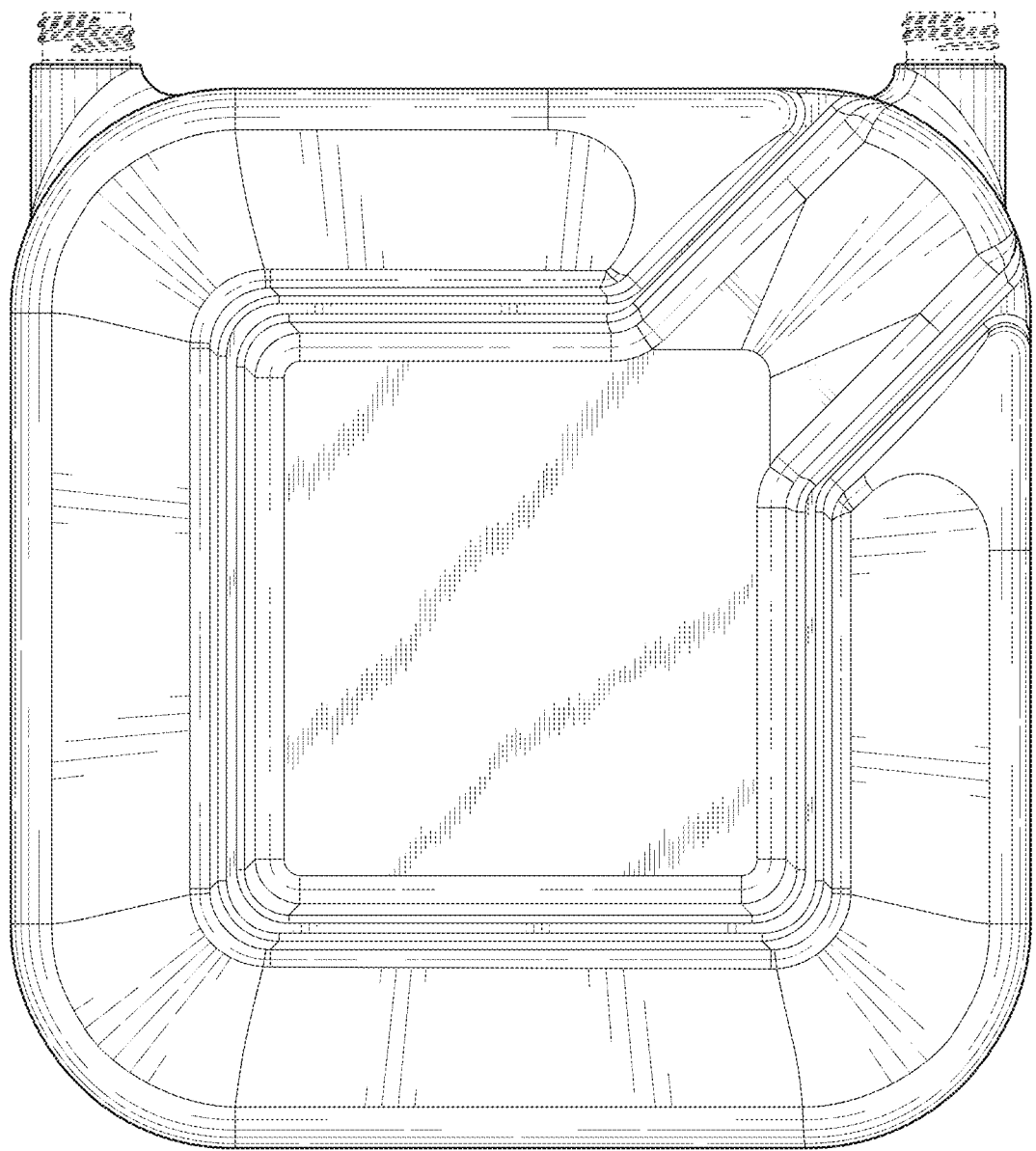
FIG. 22 is a right side elevational view of the working fluid and waste container of FIG. 5, in accordance with aspects of the present disclosure.
Figure 23:
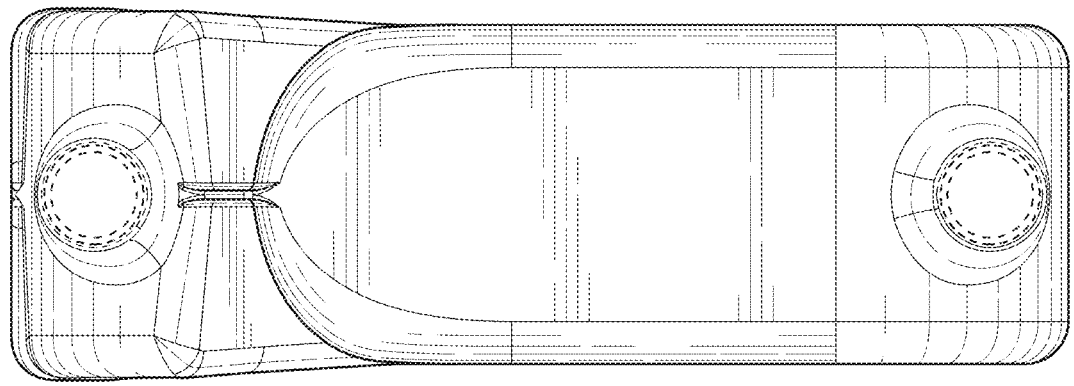
FIG. 23 is a front elevational view of the working fluid and waste container of FIG. 5, in accordance with aspects of the present disclosure.
Figure 24:
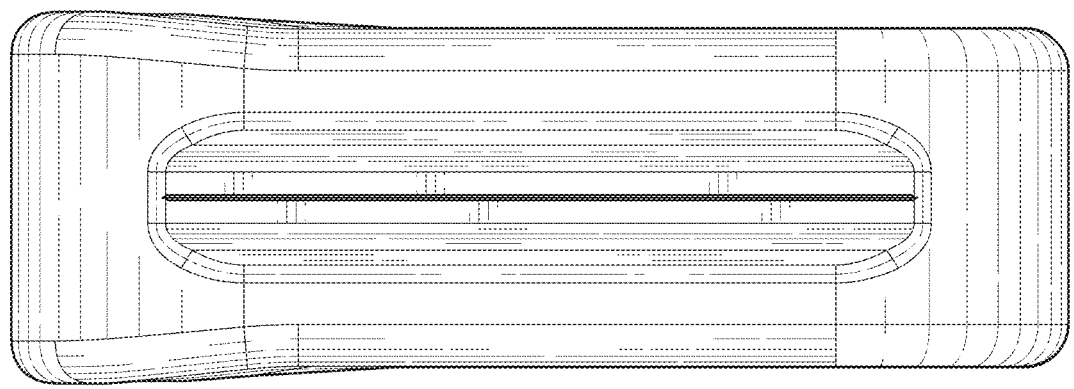
FIG. 24 is a rear elevational view of the working fluid and waste container of FIG. 5, in accordance with aspects of the present disclosure.

Accordingly, describe above are a medical diagnostic system and containers for the medical diagnostic system. FIGS. 11-17 show additional views of the reagent container of FIG. 2, with contour lines that more clearly illustrate the shape of the reagent container. In particular, FIG. 11 is a perspective view of the reagent container, FIG. 12 is a bottom plan view thereof, FIG. 13 is a top plan view thereof, FIG. 14 is a left side elevational view thereof, FIG. 15 is a right side elevational view thereof, FIG. 16 is a front elevational view thereof, and FIG. 17 is a rear elevational view thereof. FIGS. 18-24 show additional views of the working fluid and waste container of FIG. 5, with contour lines that more clearly illustrate the shape of the working fluid and waste container. In particular, FIG. 18 is a perspective view of the working fluid and waste container, FIG. 19 is a bottom plan view thereof, FIG. 20 is a top plan view thereof, FIG. 21 is a left side elevational view thereof, FIG. 22 is a right side elevational view thereof, FIG. 23 is a front elevational view thereof, and FIG. 24 is a rear elevational view thereof. The embodiments disclosed herein are merely exemplary and are not intended to limit the scope of the present disclosure.

The following describes a feature of present disclosure with reference to FIG. 1. In accordance with aspects of the present disclosure, the medical diagnostic system includes one or more cameras (not shown) for imaging encoded data-matrix codes on the reagent container 122 and the working fluid and waste container 132. The data-matrix codes on the containers 122, 132 can encode information such as expiration date, lot number, manufacturer identity, and authenticity, among other things. The camera can scan the data-matrix code to read this information, and the medical diagnostic system 100 can process and respond to the information in various ways.

In various embodiments, the larger receptacle 130 uses the camera (not shown) for imaging a data-matrix code on the working fluid and waste container 132, and the smaller receptacle 120 uses the same camera (not shown) for imaging a data-matrix code the reagent container 122. In various embodiments, the data-matrix codes are positioned on the containers 122, 132 such that the data-matrix codes can be read by the camera only when the containers 122, 132 are inserted into the medical diagnostic system 100 in a particular orientation.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in various embodiments," "in some embodiments," "in various embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may be located within a device or system at an end-user location, may be located within a device or system at a manufacturer or servicer location, or may be a cloud computing processor located at a cloud computing provider. The controller may also include a memory to store data and/or instructions that, when executed by the one or more processors, causes the one or more processors to perform one or more methods and/or algorithms.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A container configured to hold fluids usable by a medical diagnostics system, the container comprising:
    an in-use orientation in which the fluids are aspirated by the medical diagnostics system; and
    in the in-use orientation:
        a top compartment defined by an enclosed housing having a top wall, a bottom wall, side walls, and an access opening in one of the side walls, the access opening positioned adjacent to the bottom wall of the top compartment;
        a bottom compartment defined by an enclosed housing having a top wall, a bottom wall, side walls, and an access opening in one of the side walls, the access opening positioned adjacent to the bottom wall of the bottom compartment, wherein the top compartment and the bottom compartment are fluidically separate; and
        a septum between and connecting the top and bottom compartments such that the top and bottom compartments are stationary relative to each other, the septum separating the top and bottom compartments such that the walls of the top compartment do not contact the walls of the bottom compartment,
        wherein, in the in-use orientation, the top compartment is above the bottom compartment, and
        wherein at least a portion of the bottom wall of the top compartment slopes downward toward the access opening of the top compartment.

2. The container of claim 1, wherein the top wall of the bottom compartment is substantially parallel to the bottom wall of the top compartment.

3. The container of claim 1, wherein a portion of the top wall of the bottom compartment is higher than a portion of the bottom wall of the top compartment.

4. The container of claim 1, wherein a portion of the bottom wall of the top compartment is lower than a portion of the top wall of the bottom compartment.

5. The container of claim 1, wherein the septum is narrower than the top and bottom compartments.

6. The container of claim 1, wherein at least a portion of the septum is positioned halfway between the top wall of the top compartment and the bottom wall of the bottom compartment.

7. The container of claim 1, wherein at least a portion of the bottom wall of the bottom compartment slopes downward towards the access opening of the bottom compartment.

8. The container of claim 1, wherein the top compartment is smaller than the bottom compartment.

9. The container of claim 8, wherein the top compartment has a capacity between 60 mL and 130 mL.

10. The container of claim 8, wherein the bottom compartment has a capacity between 100 mL and 175 mL.

11. The container of claim 8, wherein the top compartment has a capacity between 90 mL to 100 mL, and wherein the bottom compartment holds between 130 mL and 145 mL.

12. The container of claim 1, further comprising:
    a first reagent contained in the top compartment; and
    a second reagent contained in the bottom compartment.

13. The container of claim 12, further comprising:
a first fluid seal sealing the access opening of the top compartment; and
a second fluid seal sealing the access opening of the bottom compartment,
wherein the first fluid seal and the second fluid seal are configured to be punctured by dedicated fluid access needles configured to access the first reagent and the second reagent,
wherein once punctured, the container is no longer fluid-tight.

14. The container of claim 1, further comprising a data-matrix code that encodes at least one of: expiration date, lot number, manufacturer identity, or authenticity,
wherein the data-matrix code is located on an outer surface of one of the walls of the first compartment or the second compartment.

15. A method comprising:
securing a container, holding fluids usable by a medical diagnostic system, in an in-use orientation, the in-use orientation corresponding to an orientation in which the fluids are aspirated by the medical diagnostic system, wherein in the in-use orientation, the container comprises:
a top compartment defined by an enclosed housing having a top wall, a bottom wall, side walls, and an access opening in one of the side walls, the access opening positioned adjacent to the bottom wall of the top compartment;
a bottom compartment defined by an enclosed housing having a top wall, a bottom wall, side walls, and an access opening in one of the side walls, the access opening positioned adjacent to the bottom wall of the bottom compartment, wherein the top compartment and the bottom compartment are fluidically separate; and
a septum between and connecting the top and bottom compartments such that the top and bottom compartments are stationary relative to each other, the septum separating the top and bottom compartments such that the walls of the top compartment do not contact the walls of the bottom compartment,
wherein, in the in-use orientation, the top compartment is above the bottom compartment, and
wherein at least a portion of the bottom wall of the top compartment slopes downward toward the access opening of the top compartment; and
aspirating the fluids held in the container in the in-use orientation by the medical diagnostic system.

16. The method of claim 15, wherein a portion of the top wall of the bottom compartment is higher than a portion of the bottom wall of the top compartment.

17. The method of claim 15, wherein a portion of the bottom wall of the top compartment is lower than a portion of the top wall of the bottom compartment.

18. The method of claim 15,
wherein the container further comprises a first fluid seal sealing the access opening of the top compartment and a second fluid seal sealing the access opening of the bottom compartment,
wherein the fluids held in the container in the in-use orientation are aspirated by the medical diagnostic system by a dedicated access needle for the top compartment and a dedicated access needle for the bottom compartment, and
wherein the first fluid seal and the second fluid seal are configured to be punctured by the dedicated fluid access needles and, once punctured, the container is no longer fluid-tight.

19. An apparatus comprising:
a reagent container configured to hold fluids usable by a medical diagnostics system, the reagent container comprising:
an in-use orientation in which the fluids are aspirated by the medical diagnostics system; and
in the in-use orientation:
a top compartment defined by an enclosed housing having a top wall, a bottom wall, side walls, and an access opening in one of the side walls, the access opening positioned adjacent to the bottom wall of the top compartment;
a bottom compartment defined by an enclosed housing having a top wall, a bottom wall, side walls, and an access opening in one of the side walls, the access opening positioned adjacent to the bottom wall of the bottom compartment, wherein the top compartment and the bottom compartment are fluidically separate; and
a septum between and connecting the top and bottom compartments such that the top and bottom compartments are stationary relative to each other, the septum separating the top and bottom compartments such that the walls of the top compartment do not contact the walls of the bottom compartment,
wherein, in the in-use orientation, the top compartment is above the bottom compartment; and
a working fluid and waste container configured to at least accept fluids used by the medical diagnostics system, the working fluid and waste container comprising:
a waste compartment having an access opening, an inner wall, and an outer wall, the inner wall and the outer wall having a vertical cross-section in substantially a shape of a square or rectangle with an open corner, and
a working fluid compartment having a first portion inward of the inner wall of the waste compartment and a second portion extending through the open corner, the second portion ending in an access opening of the working fluid compartment, wherein the working fluid compartment is fluidically separate from the waste compartment, and
a septum between and connecting the working fluid compartment and the waste compartment such that the working fluid compartment and the waste compartment are stationary relative to each other.

* * * * *